United States Patent [19]

Drake

[11] Patent Number: 5,057,639
[45] Date of Patent: Oct. 15, 1991

[54] DIMERIZATION PROCESS WITH SUPPORTED ELEMENTAL SODIUM CATALYST

[75] Inventor: Charles A. Drake, Nowata, Okla.

[73] Assignee: Phillips Petroleum Company, Bartlesville, Okla.

[21] Appl. No.: 611,816

[22] Filed: Nov. 13, 1990

Related U.S. Application Data

[62] Division of Ser. No. 380,574, Jul. 17, 1989, Pat. No. 4,988,658.

[51] Int. Cl.$^5$ ................................................ C07C 2/24
[52] U.S. Cl. .................................................... 585/516
[58] Field of Search ................. 585/516; 502/174, 330

[56] References Cited

U.S. PATENT DOCUMENTS

| | | | |
|---|---|---|---|
| 3,175,020 | 3/1965 | Wilkes | 585/516 |
| 3,624,177 | 11/1971 | Lowther | 585/516 |
| 3,694,379 | 9/1972 | Yamaguchi et al. | 502/243 |
| 3,759,844 | 9/1973 | Yamaguchi et al. | 502/346 |
| 4,388,480 | 6/1983 | Imai et al. | 585/516 |
| 4,520,126 | 5/1985 | Kawamoto et al. | 585/516 X |
| 4,533,781 | 8/1985 | Matsuno et al. | 585/516 |
| 4,544,790 | 10/1985 | Drake | 585/516 |
| 4,661,466 | 4/1987 | Drake et al. | 585/516 |
| 4,687,877 | 8/1987 | Bartley et al. | 585/516 |
| 4,727,213 | 2/1988 | Drake et al. | 585/516 |
| 4,810,688 | 3/1989 | Ewert et al. | 502/174 |

FOREIGN PATENT DOCUMENTS

| | | | |
|---|---|---|---|
| 7202602 | 3/1968 | Japan | 585/516 |
| 47-08043 | 3/1972 | Japan | 502/439 |
| 58-114738 | 7/1983 | Japan . | |
| 1221709 | 2/1971 | United Kingdom | 585/516 |

Primary Examiner—W. J. Shine
Assistant Examiner—D. J. McGinty
Attorney, Agent, or Firm—Lynda S. Jolly

[57] ABSTRACT

Catalyst supports, catalyst systems, methods for the preparation thereof, in dimerization processes therewith are provided. Catalyst supports are prepared from potassium carbonate, sodium carbonate, an aluminum-containing compound, and water. Catalyst systems comprise of at least one elemental alkali metal deposited on the catalyst support. Optionally, the catalyst system further comprises of at least one promoter.

12 Claims, No Drawings

DIMERIZATION PROCESS WITH SUPPORTED ELEMENTAL SODIUM CATALYST

This application is a division of application Ser. No. 380,574, filed July 17, 1989, now U.S. Pat. No. 4,988,658.

BACKGROUND OF THE INVENTION

This invention relates to alkali metal carbonate supported alkali metal catalysts.

It is known in the art to employ alkali metal carbonate supported elemental alkali metal catalysts for such conversions as propylene dimerization. Several catalyst compositions, as well as methods of preparing these types of catalysts, are known in the art. The resultant catalyst systems, although useful to dimerize olefins, do not always have a high conversion rate and/or a high isomer ratio of desired product(s) to undesired product(s). Thus, a dimerization process, because of low conversion and/or low isomer ratio, can be more time consuming and require larger, more uneconomical, reactor equipment.

SUMMARY OF THE INVENTION

It is an object of this invention to provide an improved catalyst system for the dimerization of olefins.

It is another object of this invention to provide a method to prepare an improved alkali metal carbonate supported elemental alkali metal catalyst system.

It is yet another object of this invention to provide an improved process for the dimerization of olefins.

In accordance with this invention, a dimerization catalyst comprising at least one elemental alkali metal supported on a support which comprises potassium carbonate, sodium carbonate, and at least one aluminum-containing compound is provided. This dimerization catalyst is useful to dimerize olefins and results in an improved olefin conversion rate and/or an improved isomer ratio of desired product(s) to undesired product(s).

In accordance with another embodiment of this invention, the dimerization catalyst can further comprise at least one promoter.

DESCRIPTION OF THE PREFERRED EMBODIMENTS

The present invention provides a process to prepare a catalyst support which comprises the steps of forming a thick paste comprising potassium carbonate, sodium carbonate, at least one aluminum-containing compound, and water; forming a particulate product from said paste; and calcining said particulate product. The particulate product can be formed by grinding and seiving prior to calcining, or it can be formed into an extrudate, pellets, tablets, pills, and/or any other granular form prior to calcining. After calcination, the particulate product is contacted with at least one elemental alkali metal to produce a catalyst composition.

SUPPORTS

The potassium carbonate and sodium carbonate portions of the catalyst support of the invention can be any commercially available potassium carbonate and sodium carbonate, in the form of powder, granules, or any other small particulate; larger particles, such as, for example, pellets, can be used if these larger particles are reduced to a small particulate prior to the formation of a thick paste.

The aluminum-containing compound used in the catalyst support can be any aluminum-containing compound that is convertible to aluminum oxide ($Al_2O_3$) upon calcination. Exemplary aluminum-containing compounds include, but are not limited to, alpha-alumina, gamma-alumina, hydrated alumina, e.g., hydrogilite, bialite, boehmite, diaspore, gibbsite, and Al-(OR)$_3$ wherein R is the same or different and is hydrogen and/or a linear or branched aliphatic or aromatic group having from about 1 to about 20 carbon atoms.

The amount of potassium carbonate, sodium carbonate, and aluminum-containing compound in the final, calcined support product generally comprises from about 15 to about 65 weight percent potassium carbonate, from about 5 to about 25 weight percent sodium carbonate, and from about 20 to about 80 weight percent aluminum-containing compound, based on the total weight of the calcined catalyst support. Preferably, the calcined support comprises from about 20 to about 55 weight percent potassium carbonate, from about 7 to about 22 weight percent sodium carbonate, and from about 30 to about 70 weight percent alumina, with the most preferred weight percent ranges being from about 25 to about 50 weight percent potassium carbonate, from about 10 to about 20 weight percent sodium carbonate, and from about 40 to about 60 weight percent aluminum-containing compound, in order to provide a catalyst system with improved conversion and/or improved isomer ratio.

Stated in other terms, the amount, in mass, or weight, of potassium carbonate used is from about the same as to about 7.5 times the mass of sodium carbonate used. Most preferably the amount, in mass, of potassium carbonate used is from about 1.5 to about 3 times the mass of sodium carbonate used. The mass ratio of the aluminum-containing compound to sodium carbonate is from about 1:1 to about 16:1, most preferably in the range from about 2:1 to about 6:1, for the reasons stated earlier.

The solids, potassium carbonate, sodium carbonate, and aluminum-containing compound(s) are mixed with sufficient water to form a thick paste. If too much or too little water is used, it can be difficult to form a particulate product from the thick paste. Therefore, for general guidance, a solids to water weight ratio is generally at least about 3.5 parts solids mixed with about 1 part water. However, this weight ratio can vary depending on the ease of processing thick paste for a particular product.

The thick paste is then formed into a particulate product prior to calcining. The paste can be formed into an extrudate using an extruder. The extrudate can be any diameter, but for best catalytic activity and ease of handling and processability, the extrudate is from about 1/16 to about ¼ inch in diameter. After the extrudate passes through the die, the extrudate can be cut into uniform lengths, if desired. However, uniform lengths are not always necessary, so the extrudate can be allowed to break on its own, into any length. If the extrudate is allowed to break on its own, it will usually have a length of about 2 to about 7 times the diameter width. Usually, the extrudate is allowed to break of its own accord because of ease of manufacture.

The thick paste, after drying and granulation, can also be formed into tablets using a die press, a punch press, or a pelleting machine. Tablets are usually very uniform in size. Tablets look similar to an extrudate, except the two ends of each cylindrical tablet are convex, not blunt.

The thick paste can also be formed into pellets and/or pills. Pellets and pills can be defined as any other type of form that are not prepared using an extruder, a die press, punch press, or pelleting machine. One example of an apparatus used to make pellets or pills is a disk spherudizer. A disk spherudizer, or disk pelletizer, is a flat, circular disk with a lip perpendicularly attached around the circumference of the disk. The disk is mounted at an angle and rotates; scrapers are stationarily mounted above the disk. The disk rotating speed, angle of the disk, solids feed rate onto the disk, and ratio of liquids to solids all control the diameter of the pellets. Usually, the solids and liquids are not mixed prior to introduction onto the disk, but they can be pre-mixed.

The most preferable method of forming a particulate product from the thick paste, due to ease, is to oven dry the thick paste under conditions of time and temperature sufficient to insure that substantially all of the water has been driven off. The dried paste can then be broken into pieces and fractionated by suitable means such as, for example, by passing through the appropriate mesh size screen sieves to recover a desired particle size fraction.

After formation of the particulate product, the catalyst support is dried under conditions of time and temperature sufficient so that substantially all of the water is driven off. Usually, a temperature in the range of about 80° to about 350° C., preferably a temperature in the range of about 85° to about 150° C., for at least 2 hours is sufficient. Drying can occur under any atmosphere, but for safety reasons, a vacuum oven is usually employed.

Once the catalyst support is formed and dried, it should be calcined in an oxygen-containing atmosphere at a temperature and time sufficient to partially melt the support components. Generally, temperatures in the range of about 400° to about 1200° C., preferably about 500° C. to about 1000° C., and a time of at least 2 hours are sufficient. Upon completion of calcination, the catalyst support preferably is stored in a dry atmosphere. Preferably, the catalyst support is stored under a dry, oxygen-free atmosphere until needed for further treatment.

CATALYSTS AND PROMOTERS

Catalysts systems employed in the practice of this invention comprise one of the catalyst supports described above, at least one elemental alkali metal catalyst, and optionally one or more of the following additional promoters:
  elemental copper,
  elemental cobalt,
  finely divided stainless steel,
  finely divided glass, and
  mixtures of two or more thereof.
It should be recognized, however, that the catalyst systems of the invention can contain additional components which do not adversely affect the catalyst performance, such as, for example, pigments, dyes, processing aids, inert fillers, binders and the like.

The alkali metals contemplated to be within the scope of the invention include lithium, sodium, potassium, rubidium, and cesium. While the proportion of alkali metal combined with the catalyst support can vary appreciably, generally at least about one weight percent of alkali metal based on the total weight of treated support will be employed. Generally, about 1 to about 20 weight percent alkali metal will be employed with about 2 to about 15 weight percent preferred. An alkali metal loading of about 3 to about 10 weight percent based on the total weight of treated support is most preferred for most efficient use of reagents, high catalyst activity and selectivity, high isomer ratio, and ease of catalyst preparation. Sodium is the preferred elemental alkali metal due to its ready availability as well as excellent compatibility with the inventive catalyst support.

The proportion of optional promoter on the alkali metal carbonate support can vary appreciably, but generally, at least one weight percent of the optional promoter based on the total weight of treated support will be employed. The following amounts are provided for additional guidance:

| Promoter | Loading, Weight Percent | | |
| --- | --- | --- | --- |
| | Broad | Intermediate | Preferred |
| Cu | 1–30 | 3–20 | 5–12 |
| Co | 1–50 | 3–25 | 5–15 |
| *SS | 1–80 | 3–60 | 5–50 |
| Glass | 1–50 | 2–25 | 3–15 |

**SS = Stainless Steel

The general procedure for preparation of the catalyst systems of the invention, after calcining the support, involves heating the catalyst support to a temperature in the range of about 80° to about 350° C., preferably slightly above the melting point of the particular alkali metal used, cooling the particulate support and then contacting the particulate support with at least one elemental alkali metal in a dry, oxygen-free atmosphere, such as, for example $N_2$, Ar, or the like, at a temperature sufficient to cause the alkali metal to melt. The contacting, done in an oxygen-free atmosphere, is preferably carried out with suitable mixing to ensure even distribution. Suitable temperatures for the contacting step will vary with the particular alkali metal employed. For example, with elemental potassium, temperature in the range of about 80° to 100° C. are preferred, while with elemental sodium, temperatures in the range of about 100° to 140° C. are preferred.

While the catalyst support is maintained at or above the melting point of the particular alkali metal used, in an oxygen-free atmosphere, any desired promoter(s), such as, for example, finely divided stainless steel or elemental copper, can be gradually added while the treated catalyst is continually stirred. For example, with potassium, temperatures in the range of about 80° to about 100° C. are employed. The catalyst system is then ready to be charged to the reactor.

Optionally, the catalyst support, once elemental alkali metal and any desired promoters have been deposited thereon, can be subjected to a subsequent heating step, in an oxygen-free atmosphere, to ensure as uniform a distribution as possible of the various promoters on the surface of the alkali metal carbonate support. Thus, the finished catalyst can be subjected to a temperature in the range of at least about 80° C. for a time in the range of about 0.1 to about 4 hours. A temperature in the range of about 150° to about 250° C. for a time in the range of about 0.5 to about 2 hours is presently preferred for the most uniform distribution.

Optionally, prior to charging the reactor, the catalyst system can be mixed with an inert substance to dilute the catalyst system and decrease the rate of olefin dimerization. Any inert substance which has no catalytic activity in an olefin dimerization reaction can be used. One example of such an inert substance is glass beads.

As indicated by the variety of supports, alkali metal components, and promoters included within the scope of the invention, numerous catalyst combinations are possible. Any combination of the alkali metal and optional promoters disclosed can be supported on any alkali metal carbonate support disclosed. Some possible combinations are described in detail in the examples which follow. The combination of support, alkali metal and promoter(s) which one may choose to employ will depend on a variety of variables such as for example, reactor configuration, reaction temperature and pressure, olefin feed employed, rate of olefin feed, and conversions desired.

REACTANTS

Reactants applicable for use in the process of the invention are olefinic compounds which can (a) self-react, i.e., dimerize, to give useful products such as, for example, the self-reaction of propylene gives 4-methyl-1-pentene; and/or (b) olefinic compounds which can react with other olefinic compounds, i.e., co-dimerize, to give useful products such as, for example, co-dimerization of ethylene plus propylene gives 1-pentene, co-dimerization of ethylene and 1-butene gives 3-methyl-1-pentene and so forth. As used herein, the term "dimerization" is intended to include both self-reaction and "co-dimerization" as defined above.

Suitable dimerizable olefinic compounds are those compounds having from about 3 to about 30 carbon atoms and having at least one olefinic double bond and at least one allylic hydrogen atom, i.e., at least one hydrogen atom attached to a carbon atom adjacent to a double-bonded carbon atom. Exemplary compounds include, but are not limited to, acyclic and cyclic olefins such as, for example, propylene, 1-butene, 2-butene, isobutylene, 1-pentene, 2-pentene, 1-hexene, 2-hexene, 3-hexene, 1-heptene, 2-heptene, 3-heptene, the four normal octenes, the four normal nonenes and so forth; 3-methyl-1-butene, 2-methyl-2-butene, 3-methyl-1-pentene, 3-methyl-2-pentene, 4-methyl-1-pentene, 4-methyl-2-pentene, tetramethylethylene and the like; cyclopentene, cyclohexene, methylcyclopentene, methylcyclohexene, and the like and mixtures of any two or more thereof.

Suitable co-dimerizable olefinic compounds are those compounds having from about 2 to about 30 carbon atoms, including all the compounds contemplated within the scope of "dimerizable" olefinic compounds as indicated above. In addition, olefinic compounds which do not have at least one allylic hydrogen atom are also included within the scope of co-dimerizable olefins. Exemplary compounds in addition to those indicated above, include, but are not limited to ethylene, 3,3-dimethyl-1-butene, ditertiarybutyl ethylene and the like and mixtures of any two or more thereof.

The compounds indicated above as dimerizable olefinic compounds are capable of undergoing both self-reaction, i.e., dimerization, and cross-reaction, i.e., co-dimerization, with other members of the same group or with those compounds designated as co-dimerizable. The co-dimerizable compounds which do not have at least one allylic hydrogen may be capable of isomerization to form an olefin having an allylic hydrogen under the reaction conditions employed. If such isomerization is not possible, then those non-isomerizable, co-dimerizable compounds which do not have at least one allylic hydrogen must be contacted with at least one of the "dimerizable" compounds in order to facilitate the desired co-dimerization reaction. In other words, the co-dimerizable compounds which do not have at least one allylic hydrogen atom and are not capable of isomerization to produce an olefin having at least one allylic hydrogen are therefore not capable of reacting with themselves under the reaction conditions employed for the dimerization reaction.

REACTION CONDITIONS

The dimerization reaction of the invention can be carried out using either batch or continuous types of operation, although the catalysts of the invention are particularly well suited for continuous, fixed bed, operation. Suitable equipment, such as, for example, autoclaves, tubular reactors and the like as are well known in the art can be employed. No special materials of construction are required so that steel, stainless steel, glass-lined reactors, or the like can be employed.

The reaction temperature can vary depending on the catalyst and feed(s) employed. Typically, a temperature range of about 50° to about 250° C. is suitable. Temperatures of about 80° to about 200° C. are preferred with a range of about 120° to about 170° C. most preferred because optimum reaction rates are obtained with minimum by-product formation.

The dimerization reaction can be carried out by contacting the dimerizable olefins with catalyst in the liquid phase or the gas phase, depending on the structure and molecular weight of the olefin, as well as reaction temperature and pressure employed. Pressure during the dimerization reaction can vary between wide limits. In general, higher pressures favor the progress of the reaction. Thus, pressures of atmospheric up to about 10,000 psig and higher are suitable. Preferably, pressures of about 100 to about 5,000 psig are employed, with pressures of about 1,000 to about 4,000 psig most preferred in order to achieve a good balance between reaction rate and minimize equipment and operating costs necessitated by very high reaction pressures.

If the reaction is carried out in the liquid phase, solvents or diluents for the reactants can be used. Saturated aliphatic hydrocarbons, e.g., pentane, hexane, cyclohexane, dodecane; aromatic compounds, preferably those without an alpha-hydrogen (which would be capable of undergoing alkylation under the reaction conditions) such as benzene and chlorobenzene are suitable. If the reaction is carried out in the gaseous phase, diluents such as aliphatic hydrocarbons, for example methane, ethane and/or substantially inert gases, e.g., nitrogen, argon, can be present.

The contact time required for the dimerization reaction depends upon several factors, such as, for example, the activity of the catalyst, temperature, pressure, structure of the reactants employed, level of conversion desired, and the like. The length of time during which the dimerizable olefinic compounds are contacted with catalyst can vary conveniently between about 0.1 seconds and about 24 hours although shorter and longer contact times can be employed. Preferably, times of about one minute to about 5 hours are employed. Where reaction is carried out in continuous fashion, it is convenient to express the reactant/catalyst contact time in terms of weight hourly space velocity (WHSV), i.e., the ratio of the weight of reactant which comes in contact with a given weight of catalyst per unit time. Thus, a WHSV of about 0.1 to about 10 will be employed. A WHSV of about 0.5 to about 5 is preferred, with about 1 to about 4 WHSV most preferred for optimum catalyst productivity.

PRODUCTS

The olefinic products of the invention have established utility in a wide variety of applications, such as, for example, as monomers for use in the preparation of homopolymers, copolymers, terpolymers, e.g., as the third component of ethylene-propylene terpolymers useful as synthetic elastomers, and the like.

A further understanding of the present invention and its advantages will be provided by reference to the following examples.

EXAMPLES

In each of the following examples, typically, the dimerization of propylene was carried out in a steam heated 316 stainless steel tubular reactor ($\frac{1}{2}'' \times 20''$). The catalyst system (27 grams; density about 0.84 g/mL), bounded above and below by small volumes of glass beads, was combined with 25 grams of an inert substance, i.e., no dimerization catalytic activity, to dilute the catalyst system and thus reduce and control the reaction rate. The contents of the tubular reactor were heated to the reaction temperature of about 160° C. at about 1500 psig and propylene was pumped into the reactor at a rate of about 120 mL/hr. After about 1.5 hours of reaction time and each one hour thereafter for the following 6 hours, a sample was collected and analyzed by gas liquid chromatograph (glc). The summarized results represent the analysis of the last dimerization sample collected.

Granular catalyst the part which was prepared from varying amounts of commercially available, anhydrous potassium carbonate (JT Baker, ACS reagent grade); commercially available, anhydrous sodium carbonate (JT Baker, ACS reagent grade); commercially available, anhydrous aluminum hydroxide (JT Baker, ACS reagent grade); and deionized water. The solid components had a particle size of equal to or less than about 0.42 mm (40 mesh). Sufficient water was added to the solid particles to form a thick paste. Usually, about 2 milliliters of water were added to about 1 gram of solid material. The thick paste was thoroughly mixed and then dried at about 85° C. in a vacuum oven for at least two hours in the presence of air. The dried paste was ground to about six mesh and calcined at about 600° to about 950° C. for about 2 to about 5 hours in an oxygen-containing atmosphere.

The resultant support was allowed to cool, in an oxygen-free atmosphere, to about 80° to about 85° C., at which time about 10 weight percent of elemental sodium was added. The catalyst support and catalyst system were kept under a dry, inert atmosphere during and after preparation.

Catalysts and the results of the corresponding propylene dimerizations are summarized in Table I. Propylene ($C_3=$) conversion, percent, as used in Table I, is the weight percent of reactant propylene that was converted to any type of reaction product. Selectivity, percent, data are the weight percent of product that was 4-methyl-1-pentene (4MP1). The isomer ratio, 4-methyl-1-pentene/4-methyl-2-pentene (4MP1/4MP2) is the mass ratio of 4MP1 to 4MP2 in the final product. The isomer ratio data is significant because 4MP1 and 4MP2 are difficult to separate.

TABLE I

| Run | Mass Ratio $K_2CO_3$ | Mass Ratio $Na_2CO_3$ | Al Compound | Calcine Conds. | $C_3=$ Conversion, % | 4MP1 Selectivity, % | 4MP1/ 4MP2 |
|---|---|---|---|---|---|---|---|
| 1 | 1 | — | 1, Al(OH)$_3$ | 950° C./5 hrs | 31 | 60 | 2 |
| 2 | 1.3 | — | 0.7, Al(OH)$_3$ | 950° C./5 hrs | 15 | 79 | 6 |
| 3 | 0.8 | — | 1.2, Al(OH)$_3$ | 950° C./5 hrs | 14 | 14 | — |
| 4 | 1 | — | 1, α-Al$_2$O$_3$ | 950° C./5 hrs | 11 | 87 | 17 |
| 5 | 1 | — | 1, α-Al$_2$O$_3$ | 700° C./5 hrs | 8 | 87 | 18 |
| 6 | 1 | — | 1, Boehmite | 950° C./5 hrs | 18 | 85 | 13 |
| 7 | 0.7 | 0.3 | 1, Al(OH)$_3$ | 600° C./5 hrs | 24 | 87 | 22 |
| 8 | 0.7 | 0.3 | 1, Al(OH)$_3$ | 950° C./5 hrs | 26 | 85 | 16 |
| 9 | 0.7 (KHCO$_3$) | 0.3 | 1, Al(OH)$_3$ | 950° C./5 hrs | 27 | 86 | 18 |
| 10 | 0.3 | 0.7 | 1, Al(OH)$_3$ | 950° C./5 hrs | 8 | 79 | 8 |
| 11 | 0.7 | 0.3 | 0.5, Al(OH)$_3$ 0.5, Boehmite | 950° C./5 hrs | 23 | 48 | — |
| 12 | 0.9 | 0.1 | 1, Al(OH)$_3$ | 950° C./5 hrs | 18 | 73 | 4 |
| 13 | 0.5 | 0.5 | 1, Al(OH)$_3$ | 950° C./5 hrs | 11 | 83 | 11 |
| 14 | 0.5 | 0.5 | 1, Al(OH)$_3$ | 950° C./5 hrs | 15 | 85 | 14 |
| 15 | 1.0 | 1 | 1.6, Al(OH)$_3$ | 950° C./5 hrs | 8 | 84 | 13 |
| 16 | 0.7 | 0.3 | 0.7, Al(OH)$_3$ | 950° C./5 hrs | 26 | 85 | 16 |
| 17 | 0.5 | 0.5 | 1, γ-Al$_2$O$_3$ | 950° C./5 hrs | 41 | 68 | 3 |
| 18 | 1 | — | — | 600° C./3 hrs | 8 | 77 | 6 |
| 19* | 0.5 | 0.5 | 1, Al(OH)$_3$ | 950° C./5 hrs | 6 | 88 | 27 |
| 20* | 0.5 | 0.5 | 1, Al(OH)$_3$ | 950° C./5 hrs | 6 | 76 | 15 |

*Catalyst contained 5 weight percent elemental potassium and no elemental sodium The data in Table I show that the best overall propylene dimerization catalyst is that in Runs 7 and 8, based on high levels of percent conversion, percent selectivity, and isomer ratio, although other formulations are effective propylene dimerization catalysts. Runs 1-6, where Na$_2$CO$_3$ is absent from the catalyst support, demonstrate lower percent conversions, percent selectivity, and isomer ratio. When equal mass ratios of K$_2$CO$_3$ are used, as in Runs 13, 14, and 17, the percent conversion and isomer ratio are decrease; the percent conversion in Run 17 appears to be an unreproducible anomaly. Use of elemental potassium as the active catalytic component, as in Runs 19 and 20, has a detrimental effect on percent conversion.

The examples have been provided merely to illustrate the practice of the invention and should not be read so as to limit the scope of the invention or the appended claims in any way. Reasonable variations and modifications, not departing from the essence and spirit of the invention, are contemplated to be within the scope of patent protection desired and sought.

I claimed is:

1. A process for the dimerization of at least one dimerizable olefin which comprises contacting said olefin under dimerization conditions with a catalyst system comprising:
   (a) elemental sodium; and
   (b) a support comprising potassium carbonate within the range of about 15 to about 65 weight percent, sodium carbonate within the range of about 5 to about 25 weight percent, and at least one aluminum-containing compound within the range of about 20 to about 80 weight percent, all based on the total weight of the support;
   wherein component (a) is supported on component (b).

2. A process according to claim 1 wherein said contacting is carried out at a temperature within the range of about 50° to about 250° C., a pressure within the range of about 100 to about 10,000 psig, and a weight hourly space velocity within the range of about 0.1 to about 10.

3. A process according to claim 1 wherein said elemental sodium is about 1 to about 20 weight percent of said composition.

4. A process according to claim 1 wherein said aluminum-containing compound is oxidizable to aluminum oxide.

5. A process according to claim 4 wherein said aluminum-containing compound is selected from the group consisting of alumina hydrates, alpha-alumina, gamma-alumina, and mixtures thereof.

6. A process according to claim 1 wherein said catalyst system further comprises a promoter selected from the group consisting of elemental copper, elemental cobalt, finely divided stainless steel, finely divided glass, and mixtures thereof.

7. A process for the production of 4-methyl-1-pentene which comprises contacting propylene under dimerization conditions with a catalyst system comprising:
   (a) elemental sodium; and
   (b) a support comprising potassium carbonate within the range of about 15 to about 65 weight percent, sodium carbonate within the range of about 5 to about 25 weight percent, and at least one aluminum-containing compound within the range of about 20 to about 80 weight percent, all based on the total weight of the support;
   wherein component (a) is supported on component (b).

8. A process according to claim 7 wherein said contacting is carried out at a temperature within the range of about 80° to about 200° C., a pressure within the range of about 1000 to about 4000 psig, and a weight hourly space velocity within the range of about 0.1 to about 10.

9. A process according to claim 7 wherein said elemental sodium is about 1 to about 20 weight percent of said composition.

10. A process according to claim 1 wherein said aluminum-containing compound is oxidizable to aluminum oxide.

11. A process according to claim 10 wherein said aluminum-containing compound is selected from the group consisting of alumina hydrates, alpha-alumina, gamma-alumina, and mixtures thereof.

12. A process according to claim 7 wherein said catalyst system further comprises a promoter selected from the group consisting of finely divided stainless steel, elemental copper, elemental cobalt, finely divided glass, and mixtures thereof.

* * * * *